United States Patent [19]

Hsu et al.

[11] Patent Number: 5,688,524
[45] Date of Patent: Nov. 18, 1997

[54] TRANSDERMAL FORMULATIONS FOR ADMINISTERING PRAZOSIN

[75] Inventors: Tsung-Min Hsu, Union City; Eric J. Roos, Menlo Park, both of Calif.

[73] Assignee: Cygnus, Inc., Redwood City, Calif.

[21] Appl. No.: 28,888

[22] Filed: Mar. 10, 1993

Related U.S. Application Data

[63] Continuation-in-part of Ser. No. 750,570, Aug. 27, 1991, abandoned.

[51] Int. Cl.$^6$ ............................................. A61F 13/00
[52] U.S. Cl. ........................... 424/449; 424/448; 514/946; 514/947
[58] Field of Search ................................ 424/448, 449; 514/946, 947

[56] References Cited

U.S. PATENT DOCUMENTS

| | | | |
|---|---|---|---|
| 4,762,851 | 8/1988 | Alexander et al. | 514/420 |
| 4,820,720 | 4/1989 | Sanders et al. | 514/946 |
| 4,847,250 | 7/1989 | Alexander et al. | 514/247 |
| 4,970,206 | 11/1990 | Alexander et al. | 514/174 |
| 5,118,845 | 6/1992 | Peck et al. | 424/448 |
| 5,474,783 | 12/1995 | Miranda | 424/448 |

FOREIGN PATENT DOCUMENTS

| | | |
|---|---|---|
| 61-178915 | 8/1986 | Japan. |
| 2202813 | 8/1990 | Japan. |
| 2142237 | 1/1985 | United Kingdom. |

OTHER PUBLICATIONS

Katz et al., "Enhanced skin permeation of Prazosin by transcutol–oleic acid mixture" *Proceed. Intern. Symp. Control. Rel. Bioact. Mater.*, Controlled Release Society, Inc., (1991) 18:533–534.

Tenjarla, S.N., "Transdermal drug delivery of Prazosin" *Pharm. Res.* (1990) 7(9):S–189 (abstract No. PDD7312).

*Primary Examiner*—D. Gabrielle Phelan
*Attorney, Agent, or Firm*—Morrison & Foerster LLP

[57] ABSTRACT

Prazosin is formulated in solution with a skin permeation enhancer composition of: a sulfhydryl-containing compound, a fatty acid eater, and a polar solvent for transdermal administration to treat hypertension or benign prostatic hypertrophy. The formulation is employed in the form of a skin patch comprising (a) an impermeable backing layer, (b) a reservoir of the prazosin-enhancer solution, (c) a porous support member that retains the solution but is not a permeation barrier to the solution, a peripheral adhesive layer for affixing the patch to the skin, and a release liner layer.

16 Claims, 1 Drawing Sheet

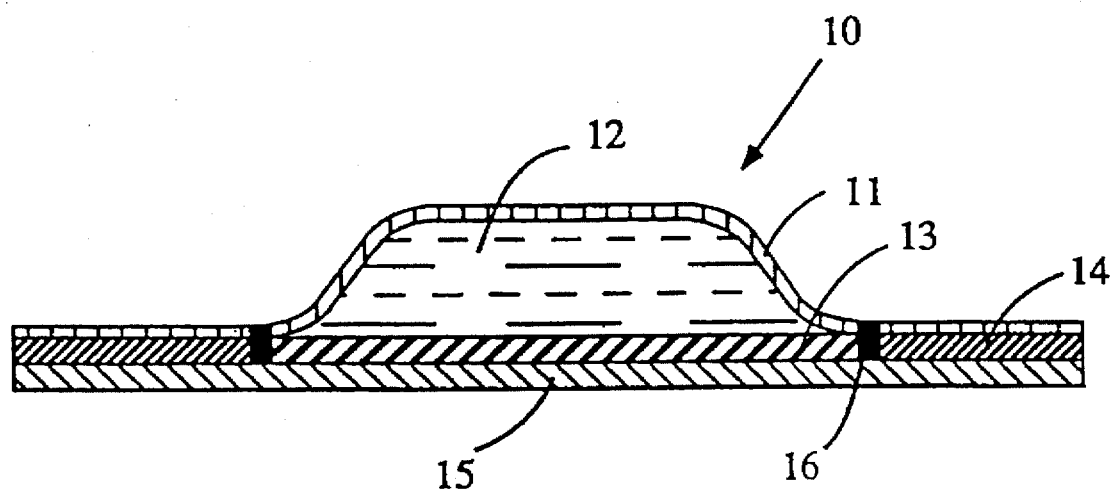

TRANSDERMAL FORMULATIONS FOR ADMINISTERING PRAZOSIN

CROSS-REFERENCE TO RELATED APPLICATION

This application is a continuation-in-part of U.S. application Ser. No. 07/750,570, filed 27 Aug. 1991, now abandoned, the entire disclosure of which is incorporated herein by reference.

DESCRIPTION

1. Technical Field

This invention relates to methods and formulations for administering the drug prazosin transdermally.

2. Background

Prazosin is an antihypertensive drug that appears to produce its antihypertensive effect by relaxation of peripheral arterioles as a consequence of postsynaptic α-adrenoreceptor blockade. Recent studies have also shown prazosin to be effective in treating benign prostatic hypertrophy (BPH), a chronic bladder outflow obstruction commonly occurring in aging males. The effect of prazosin on BPH is apparently due to decreasing the resistance along the prostatic urethra by relaxing the smooth muscle of the prostate.

Prazosin has a relatively short half-life which requires that it be administered several times per day by the oral route. Orally administered prazosin has incomplete bioavailability that is caused by incomplete absorption, degradation in the gastrointestinal tract, and first pass liver metabolism. These properties make prazosin candidate for transdermal administration. In this regard, available data indicate target transdermal delivery rates of approximately 10 $\mu g/cm^2/hr$ through 20 $cm^2$ of skin to achieve levels needed for hypertension therapy and approximately one-quarter of that rate for BPH therapy.

There are several prior publications relating to transdermal administration of prazosin. Japanese Patent Pub. No. 61178915 proposed formulations of prazosin hydrochloride which contain polypropylene glycol, polyethylene glycol, lecithin, urea, amino acids, or 1-dodecylhexahydro-2H-azepine 2-one (Azone) as permeation enhancers. Japanese Patent Publ. No. 2202813 relates to the use of $C_{1-18}$ alkyl esters of gallic acid as percutaneous permeation enhancers and lists prazosin hydrochloride among the drugs that may be combined therewith. Similarly, U.S. Pat. Nos. 4,847,250 and 4,970,206 suggest that transdermal administration of prazosin be enhanced with pyroglutamic acid esters.

Katz, D., and Touitou, E., *Proc. Int. Symp. Control. Rel. Bioact. Material* (1991) Vol. 18, describes studies of the flux of prazosin hydrochloride through rabbit ear skin from twelve different formulations. Those formulations containing oleic acid and/or Transcutol exhibited the highest flux.

Finally, Tenjarla, S. N. *Pharm. Res.* (1990) Vol. 7, No. 9, S-189, reports that prazosin (PZ) flux through human skin (formulation not identified) was 1.6 $\mu g/cm^2/hr$ and that "with a suitable chemical enhancer, transdermal delivery of PZ appears promising."

An object of this invention is to provide a transdermal prazosin formulation that provides prazosin at the rates required for hypertension and/or BPH therapy.

DISCLOSURE OF THE INVENTION

One aspect of the invention is a method for administering prazosin to an individual in therapeutically effective amounts comprising administering prazosin transdermally to the individual in combination with a skin permeation enhancer composition comprising (a) a nontoxic sulfhydryl-containing compound, (b) a nontoxic fatty acid ester; and (c) a nontoxic polar solvent to an area of unbroken skin of about 20 to about 60 $cm^2$ over a prolonged period at a rate that provides at least about 50 μg prazosin per hour.

Another aspect of the invention is a formulation of prazosin for transdermal administration comprising a therapeutically effective amount of prazosin in combination with an effective amount of a skin permeation enhancer composition comprising (a) a nontoxic sulfhydryl-containing compound, (b) a nontoxic fatty acid ester, and (c) a nontoxic polar solvent.

A further aspect of the invention is a skin patch for administering prazosin transdermally in therapeutically effective amounts over a prolonged period comprising in combination (a) an impermeable backing layer;

(b) a reservoir of a solution of prazosin in a skin permeation enhancer composition comprising:

(i) a nontoxic sulfhydryl-containing compound;

(ii) a nontoxic fatty acid ester; and (iii) a nontoxic polar solvent;

(c) a porous support member underlying the reservoir that retains the solution but is not a substantial permeation barrier to the solution; and (d) means for affixing the patch to the skin, said patch having an effective basal surface area of about 20 to 60 $cm^2$ and providing a prazosin skin flux via said effective basal surface area of at least about 50 μg/hr over said period.

BRIEF DESCRIPTION OF THE DRAWING

The drawing shows a crosssectional view of an embodiment of a skin patch for administering prazosin transdermally according to the present invention.

MODE FOR CARRYING OUT THE INVENTION

As used herein, the term "transdermal" intends passage of prazosin through unbroken human skin into circulation.

As used herein, the term "therapeutically effective amount" intends that dose of prazosin that provides the desired therapy. In the case of treating BPH, that dose will usually be in the range of 0.5 to 5 mg/day, more usually 1.5 to 4 mg/day; whereas for treating hypertension, the dose will usually be about 2 to 20 mg/day, more usually 6 to 15 mg/day.

"Skin flux" as used herein intends the rate of passage of prazosin through a defined area of skin as measured in vitro by the procedure described in Example 1, infra.

The term "effective basal surface area" intends the surface area of the patch that is in contact with the skin and through which prazosin is transmitted to the skin.

The term "nontoxic" means that the compound referred to does not damage the skin or cause intolerable levels of skin irritation.

"Prazosin" intends the free base form of the drug as well as pharmaceutically acceptable salts thereof.

A "prolonged period" intends a period of at least about 1 day, typically a multiday period of 3 to 7 days.

The enhancer composition that is used in combination with prazosin according to the invention comprises: a sulfhydryl-containing organic compound, a fatty acid ester, and a polar solvent. The sulfhydryl-containing compound preferably contains a single —SH group. Examples of suitable sulfhydryl-containing compounds arm N-(2-mercaptopropionyl)glycine, thioglycerol, thioacetic acid, thiosalicylic acid, bucillamine (N-2-mercapto-2-methyl-1-oxopropyl)L-cysteine), acetylcysteine, and mercaptomenthone. The sulfhydryl-containing compound will typically constitute 1% to 25% by weight of the enhancer composition, preferably 2% to 10% by weight. Compounds such as glutathione/NaOH, ethylene diamine tetracetic acid (EDTA)/NaOH, or other reducing agents may be added to the enhancer composition to prevent oxidation of the sulfhydryl-containing component.

The meter component of the enhancer composition will normally be a compound of the formula

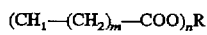

$(CH_1—(CH_2)_m—COO)_nR$ where m is an integer from 8 to 16, preferably to 12, inclusive, n is 1 or 2, and R is alkyl of 1 to 3 carbon atoms, inclusive, substituted with 0 to 2 hydroxyl groups, inclusive. The preferred esters of this formula arm hydroxyalkyl esters of lauric acid, with propylene glycol monolaurate (PGML) being particularly preferred. The ester will normally constitute 5% to 80% by weight of the enhancer composition.

The polar solvent will normally constitute 10% to 90% by weight of the enhancer composition. Examples of polar solvent that may be used are ethanol, propylene glycol (PG), N-methyl-2-pyrrolidone (M-pyrol), benzyl alcohol, 1,4-butanediol, 1,3-butanediol, 2,3-butanediol, 1,5-pentanmdiol, Transcutol (disthyleneglycol monoethyl ether), nnd low molecular weight polyethylene glycol (<500 m.w.)

The prazosin will usually be mixed with the enhancer composition in amounts in the range of about 5 to 200 mg.

The drawing illustrates an embodiment of a skin patch for administering prazosin transdermally. The patch generally designated 10, comprises: an impermeable backing layer 11; a prazosin-enhancer-solution reservoir 12; a porous support member 13 underlying the reservoir; a peripheral adhesive layer 14; and a release liner layer 15. The backing is heat sealed to the porous support member 13 at 16 about the periphery of the reservoir.

The backing layer 11 functions as the primary structural element of the device and provides the device with much of its mechanical (e.g., flexibility, etc.) properties. It also serves as a protective covering to prevent loss of prazosin/enhancer via transmission through the upper surface of the device. Backing 11 is preferably made of a sheet or film of polymer or a polymer-metal film laminate that is substantially impermeable to prazosin and the enhancer composition. The layer is preferably on the order of 0.1 to 0.2 mm in thickness. Examples of suitable backing materials are styrene-isoprene-styrene block copolymer, polyurethane-polyisobutene-polyurethane laminate, styrene-ethylene-butylene-styrene copolymer.

The support member 13 is a highly porous member that retains the liquid formulation within the reservoir (i.e., it deters bulk flow of the formulation out of the reservoir, but does not deter permeation and diffusion of the formulation from the reservoir into the skin). Nonwoven fabrics such as nonwoven polyester, polyethylene, polypropylene, and other synthetic polymers may be used. The basal surface of the nonwoven fabric may be impregnated with a pharmaceutically acceptable pressure-sensitive adhesive to facilitate the contact of that surface with the skin. The material from which member 13 is made should be heat- or otherwise sealable to the backing member to provide a barrier to transverse flow of solution from the reservoir. The basis weight of the support member 13 will usually be 0.001 to 0.003 g/cm².

The peripheral adhesive layer 14 is the means by which the patch is affixed to the skin. This layer is made from a pharmaceutically acceptable pressure sensitive adhesive polymer much as polydimethylsiloxane (Silicone), polyimobutene, polyacrylate, polyurethane, low molecular weight polyether block amide copolymers (PEBAX copolymers), tacky rubbers such as polystyrene-isoprene copolymers, polystyrene-butadiene copolymers, and the like. The thickness of this layer will be in the mama range as that of the support member, i.e., about 40 to 100 microns.

Prior to use, device 10 includes a release liner 15. Just prior to use, this layer is removed from the device to expose contact adhesive layer 14. The release liner will normally be made from a drug/vehicle/enhancer impermeable material (e.g., polyethylene terephthalate or other polyesters) that is inherently "strippable" or rendered so by techniques such as silicone or fluorocarbon treatment.

The following example, further illustrate the invention. These examples are not intended to limit the invention in any manner.

EXAMPLE 1

In Vitro Skin Flux of Prazosin Free Base from Various Liquid Formulations
Skin Permeation Studies Human cadaver skin was used for skin flux studies, Frozen skin was thawed and epidermal layers (stratum corneum and viable epidermis) separated from the full-thickness skin by immersion in water at 60° C. for 2 minutes. The epidermis was mounted carefully between the two halves of modified Franz cells. The receiver compartment was filled with pH 5 phosphate buffer. Five hundred µl of the candidate formulations (saturated with prazosin free base) were then added into the donor compartment to initiate the skin flux experiments. The temperature of the diffusion cell contents was maintained at 32° C. At a predetermined time, a 1 ml aliquot was withdrawn from the receiver and replaced with fresh buffer. Samples were assayed by HPLC using a UV-detector at 254 nm. Adequate chromatographic resolution was achieved using a Brown-Lee RP-IB column. The mobile phase was 30% acetonitrile—70% 0.025N phosphate buffer, pH 5.0 into which 2 mg/L triethanol amine (TEA) was added: The retention time was 2.5–3.2 minutes. The skin flux (µg/cm²/hr) was determined from the steady-state slope of a plot of cumulative amount of prazosin permeated through the skin versus time.

Results

The results of these studies are reported in Table 1 below.

TABLE 1

In Vitro Skin Flux of Prazosin Freebase From Vehicles

| Vehicles | Flux (µg/cm⁷/hr) |
|---|---|
| H₂O | n/a* |
| PG | n/a |
| Transcutol | n/a |
| PGML | 0.05 ± 0.02 |
| 40% oleic acid, 60% EtOH | 0.20 ± 0.05 |
| 40% PGML, 60% EtOH | 0.44 ± 0.01 |
| 40% oleic acid, 60% PGML | 0.12 ± 0.03 |
| 100% Thioglycerol | n/a |
| 40% Thioglycerol, 60% EtOH | 0.39 ± 0.33 |

TABLE 1-continued

In Vitro Skin Flux of Prazosin Freebase From Vehicles

| Vehicles | Flux (μg/cm$^2$/hr) |
| --- | --- |
| 40% Thioglycerol, 60% H$_2$O | 0.04 ± 0.01 |
| 20% transcutol, 80% PGML | 0.10 ± 0.02 |
| 50% Thioglycerol, 33% PGML, 17% EtOH | 6.63 ± 0.59 |
| 25% Thioglycerol, 25% PGML, 50% EtOH | 30.6 ± 1.0 |
| 25% N-(2-mercaptopropionyl)glycine, 25% PGML, 50% EtOH | 31.8 ± 10.9 |
| 10% N-(2-mercaptopropionyl)glycine, 25% PGML, 65% EtOH | 11.1 ± 3.92 |
| 5% N-(2-mercaptopropionyl)glycine, 25% PGML, 70% EtOH; | 4.54 ± 2.20 |
| 40% PG, 40% PGML, 20% benzyl alcohol | 5.05 ± 3.96 |
| 25% N-(2-mercaptopropionyl)glycine, 25% PGML, 70% EtOH | 8.67 ± 0.74 |
| 5% N-(2-mercaptopropionyl)glycine, 10% TEA, 1% Glutahione, 60% PG, 29% PGML | 7.48 ± 0.20 |
| 2% N-(2-mercaptopropionyl)glycine, 10% PGML, 88% PG, 40 mg/ml base | 11.5 ± 3.6 |
| 5% N-(2-mercaptopropionyl)glycine, 25% PGML, 70% PG, saturated | 9.3 ± 2.6 |
| 5% N-(2-mercaptopropionyl)glycine, 25% PGML, 70% EtOH, saturated | 12.8 ± 5.1 |
| 2% N-(2-mercaptopropionyl)glycine, 10% PCML 88% PG, saturated | 14.6 ± 1.5 |
| 5% N-(2-mercaptopropionyl)glycine, 70% EtOH, 25% PGML, saturated | 18.5 ± 7.9 |
| 5% N-(2-mercaptopropionyl)glycine, 70% PG, 25% PGML, saturated | 20.4 ± 4.6 |
| 60% EtOH, 40% Capric acid, base sat. | 3.3 ± 0.5 |
| 60% Benzyl Alcohol, 40% PGML | 1.1 ± 0.5 |

*n/a = Skin flux values were below 0.01 μg/cm$^3$/hr

As indicated in Table 1, the only formulations that provided practical fluxes were those that contained a sulfhydryl compound, a fatty acid meter, and a polar solvent. Rabbit skin irritation studies indicated that the formulation containing 5% N-(2-mercapto propionyl)glycins exhibited the lowest skin irritation of those formulations exhibiting practical fluxes. For that reason, the 5% tiopronin formulations are preferred.

EXAMPLE 2

In Vitro Skin Flux of Prazosin Hydrochloride from Liquid Formulations

Skin flux studies were carried out as in Example 1 on candidate formulations of prazosin hydrochloride (at saturation). The results of these studies are reported in Table 2 below.

TABLE 2

In Vitro Skin Flux of Prazosin HCl in Various Vehicles

| Vehicles | Flux (μg/cm$^2$/hr) |
| --- | --- |
| H$_2$O | 0.04 ± 0.01 |
| EtOH | 0.01 ± 0.01 |
| 40% Oleic acid, 60% EtOH | 0.36 ± 0.02 |
| 40% PGML, 60% EtOH | 0.41 ± 0.02 |
| 40% Thioglycerol, 60% EtOH | 1.80 ± 0.50 |
| 50% Thioglycerol, 33% PGML, 17% EtOH | 11.90 ± 4.50 |

EXAMPLE 3

In Vitro Skin Flux of Prazosin Free Base from a Liquid Reservoir-Type Skin Patch Skin Flux Methodology A simulated reservoir system was arranged in such a way that a membrane of a solvent based acrylate adhesive (Morstik 709)/non-woven support was mounted on the epidermis and then placed between the two halves of modified Franz cell. The adhesive/non-woven support membrane was prepared by impregnating the adhesive polymer solution into the non-woven support mounted on a release liner and then drawing down the polymer solution through the non-woven support with a 1–3 mil casting knife to form a thin layer membrane. The membrane was placed on the skin with the release liner removed. On the top of the membrane, a candidate formulation (saturated with prazosin) was added to initiate the skin flux study. The remainder of the study was carried out as an Example 1.

Results

The results of these studies are reported in Table 3 below.

TABLE 3

| Formulation | Flux (μg/cm$^2$/hr) |
| --- | --- |
| 5% N-(2-mercaptopropionyl)glycine, 29% PGML, 50% EtOH, 4% PG, 10% 3N, NaOH, 2% EDTA (pH 6.5) | 6.97 ± 3.50 |
| 5% N-(2-mercaptopropionyl)glycine, 29% PGML, 5% EtOH, 4% PG, 2% gluthaion, 10% 3N NaOH (pH 5.0) | 5.92 ± 1.20 |
| 5% N-(2-mercaptopropionyl)glycine, 38% PGML, 57% EtOH (pH 3.0) | 2.40 ± 0.40 |
| 5% N-(2-mercaptopropionyl)glycine, 5% TEA, 1% glutathione, 74% PG, 14% PGML | 5.6 ± 0.7 |
| 5% N-(2-mercaptopropionyl)glycine, 20% PGML, 75% M-pyrol | 10.9 ± 0.9 |
| 15% M-pyrol, 10% PGML, 60% EtOH, 5% N-(2-mercaptopropionyl)glycine, 10% 2N NaOH | 9.1 ± 3.7 |
| 5% N-(2-mercaptopropionyl)glycine, 10% 2N NaOH; 2.5% glutathione, 5.5% PG, 65% EtOH, 14% PGML (pH 6.0) | 4.6 ± 0.8 |

Modifications of the above-described modes for carrying out the invention that are obvious to those of skill in the fields of chemistry, transdermal drug delivery, and related fields are intended to be within the scope of the following claims.

We claim:

1. A method for administering prazosin to an individual in therapeutically effective amounts comprising administering prazosin transdermally to the individual over a prolonged period in combination with a skin permeation enhancer composition comprising (a) at least one nontoxic sulfhydryl-containing compound from the group of N-(2-mercaptopropionyl)glycine, thioglycerol, thioacetic acid, thiosalicylic acid, bucillamine, acetylcysteine and mercaptomenthone, (b) a nontoxic fatty acid ester;

(c) a nontoxic polar solvent to an area of unbroken skin of about 20 to about 60 cm$^2$ over said period at a rate that provides at least about 50 μg prazosin per hour to the individual.

2. The method of claim 1 wherein the fatty acid ester is of the formula

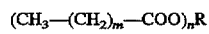

where m is an integer from 8 to 16, preferably 8 to 12, inclusive, n is 1 or 2, and R is alkyl of 1 to 3 carbon atoms, inclusive, substituted with 0 to 2 hydroxyl groups, inclusive, and the polar solvent is ethanol, propylene glycol, N-methyl-2-pyrrolidone, benzyl alcohol, 1,4-butanediol, and 1,5-pentanediol.

3. The method of claim 1 wherein the sulfhydryl-containing compound is N-(2-mercaptopropionyl)glycine, the polar solvent is ethanol or propylene glycol, and the fatty acid ester is propylene glycol monolaurate.

4. The method of claim 1 wherein the sulfhydryl-containing compound constitutes 1 to 25% by weight of the enhancer composition, the fatty acid ester constitutes 5 to 80% of the enhancer composition, and the polar solvent constitutes 10 to 90% of the enhancer composition.

5. The method of claim 1 wherein the prazosin is being administered to a male individual to treat benign prostatic hypertrophy.

6. The method of claim 1 wherein the prazosin is being administered to treat hypertension and the rate provides at least about 200 µg/hr to the individual.

7. A formulation of prazosin for transdermal administration comprising a therapeutically effective amount of prazosin in combination with a skin permeation enhancer composition comprising (a) at least one nontoxic sulfhydryl-containing compound from the group of N-(2-mercaptopropionyl)glycine, thioglycerol, thioacetic acid, thiosalicylic acid, bucillamine, acetylcysteine and mercaptomenthone, (b) a nontoxic fatty acid ester, and (c) a nontoxic polar solvent.

8. The formulation of claim 7 wherein the fatty acid ester is of the formula $$(CH_3-(CH_2)_m-COO)_nR$$

where m is an integer from 8 to 16, preferably 8 to 12, inclusive, n is 1 or 2, and R is alkyl or 1 to 3 carbon atoms, inclusive, substituted with 0 to 2 hydroxyl groups, inclusive, and the polar solvent is ethanol, propylene glycol, N-methyl-2-pyrrolidone, benzyl alcohol, 1,4-butanediol, or 1,5-pentanediol.

9. The formulation of claim 7 wherein the sulfhydryl-containing compound is N-(2-mercaptopropionyl)glycine, the polar solvent is ethanol or propylene glycol, and the fatty acid ester is propylene glycol monolaurate.

10. The formulation of claim 7 wherein the sulfhydryl-containing compound constitutes 1 to 25% by weight of the enhancer composition, the fatty acid ester constitutes 5 to 80% of the enhancer composition, and the polar solvent constitutes 10 to 90% of the enhancer composition.

11. A skin patch for administering prazosin transdermally in therapeutically effective amounts over a prolonged period comprising in combination (a) an impermeable backing layer;

(b) a reservoir of a solution of prazosin in a skin permeation enhancer composition comprising:
  (i) at least one nontoxic sulfhydryl-containing compound from the group of N-(2-mercaptopropionyl) glycine, thioglycerol, thioacetic acid, thiosalicylic acid, bucillamine, acetylcysteine and mercaptomenthone,
  (ii) a nontoxic fatty acid ester;
  (iii) a nontoxic polar solvent;

(c) a porous support member underlying the reservoir that retains the solution but is not a substantial permeation barrier to the solution; and (d) means for affixing the patch to the skin, said patch having an effective basal surface area of about 20 to 60 $cm^2$ and providing prazosin skin flux via said effective basal surface area of at least about 50 µg/hr over said period.

12. The skin patch of claim 11 wherein the fatty acid ester is of the formula $$(CH_3-(CH_2)_m-COO)_nR$$

where m is an integer from 8 to 16, preferably 8 to 12, inclusive, n is 1 or 2, and R is alkyl of 1 to 3 carbon atoms, inclusive, substituted with 0 to 2 hydroxyl groups, inclusive, and the polar solvent is ethanol, propylene glycol, N-methyl-2-pyrrolidone, benzyl alcohol, 1,4-butanediol, and 1,5-pentanediol.

13. The skin patch of claim 11 wherein the sulfhydryl-containing compound is N-(2-mercaptopropionyl)glycine, the polar solvent is ethanol or propylene glycol, end the fatty acid ester is propylene glycol monolaurate.

14. The skin patch of claim 11 wherein the sulfhydryl-containing compound constitute, 1 to 25% by weight of the enhancer composition, the fatty acid ester constitutes 5 to 80% or the enhancer composition, end the polar solvent constitutes 10 to 90% of the enhancer composition.

15. The skin patch of claim 11 wherein the prazosin is being administered to a male individual to treat benign prostatic hypertrophy.

16. The skin patch of claim 11 wherein the prazosin is being administered to treat hypertension and the rate provides at least about 200 µg/hr to the individual.

* * * * *

UNITED STATES PATENT AND TRADEMARK OFFICE
CERTIFICATE OF CORRECTION

PATENT NO. : 5,688,524

DATED : November 18, 1997

INVENTOR(S) : Tsung-Min Hsu and Eric J. Roos

It is certified that error appears in the above-indentified patent and that said Letters Patent is hereby corrected as shown below:

TITLE PAGE:

In the references cited, ref. 2, "514/946" should be --514/356--
ref. 6, "424/448" should be --564/215--

In the Abstract, line 1, "akin" should be --skin--
line 3, "eater" should be --ester--

Column 1, line 32, after "prazosin" insert --a--

Column 3, line 2, "arm" should be --are--
line 13, "meter" should be --ester--
line 16, "$CH_1$" should be --$CH_3$--
line 18, after "preferably" insert --8--
line 21, "arm" should be --are--
line 30, "pentanmdiol" should be --pentanediol--
line 30, "disthyleneglycol" should be --diethyleneglycol--
line 31, "nnd" should be --and--
line 61, "polyester" should be --polyesters--

Column 4, line 7, "much" should be --such--
line 8, "polyimobutene" should be --polyisobutene--
line 12, "mama" should be --same--
line 44, "IB" should be --18--
line 58, "$cm^7$" should be --$cm^2$--

UNITED STATES PATENT AND TRADEMARK OFFICE
CERTIFICATE OF CORRECTION

PATENT NO. : 5,688,524
DATED : November 18, 1997
INVENTOR(S) : Tsung-Min Hsu and Eric J. Roos It is certified that error appears in the above-indentified patent and that said Letters Patent is hereby corrected as shown below:

Column 5, line 5, "$cm^7$" should be --$cm^2$--
  line 9, "6.63" should be --6.43--
  line 33, ", "$cm^7$" should be --$cm^2$--
  line 39, "mercapto propionyl" should be --mercaptopropionyl--
  line 39, "glycins" should be --glycine--

Column 7, line 34, "$CH_1$" should be --$CH_3$--
  line 37, "or" (second occurrence) should be --of--

Column 8, line 39, "constitute" should be --constitutes--
  line 41, "end" should be --and--

Signed and Sealed this

Fourth Day of August, 1998

*Attest:*

BRUCE LEHMAN

*Attesting Officer*    *Commissioner of Patents and Trademarks*